(12) United States Patent
Maier et al.

(10) Patent No.: US 10,779,978 B2
(45) Date of Patent: Sep. 22, 2020

(54) STENT DELIVERY SYSTEM

(71) Applicant: Joline GmbH & Co. KG, Hechingen (DE)

(72) Inventors: Jan Maier, Moessingen (DE); Gerd Eisold, Grosselfingen (DE)

(73) Assignee: Joline GmbH & Co. KG, Hechingen (DE)

( * ) Notice: Subject to any disclaimer, the term of this patent is extended or adjusted under 35 U.S.C. 154(b) by 237 days.

(21) Appl. No.: 16/075,064

(22) PCT Filed: Feb. 16, 2017

(86) PCT No.: PCT/EP2017/053490
§ 371 (c)(1),
(2) Date: Aug. 2, 2018

(87) PCT Pub. No.: WO2017/140772
PCT Pub. Date: Aug. 24, 2017

(65) Prior Publication Data
US 2019/0046344 A1    Feb. 14, 2019

(30) Foreign Application Priority Data

Feb. 19, 2016    (DE) .................. 10 2016 102 990
Aug. 18, 2016    (DE) .................. 10 2016 115 351

(51) Int. Cl.
*A61F 2/966*    (2013.01)
*A61F 2/95*    (2013.01)

(52) U.S. Cl.
CPC ............ *A61F 2/966* (2013.01); *A61F 2/9517* (2020.05); *A61F 2002/9665* (2013.01)

(58) Field of Classification Search
CPC .......... A61F 2/95; A61F 2/9517; A61F 2/962; A61F 2/966; A61F 9/0017; A61F 2002/9665

See application file for complete search history.

(56) References Cited

U.S. PATENT DOCUMENTS

2007/0270932 A1    11/2007    Headley et al.
2014/0135909 A1    5/2014    Carr et al.
2014/0180380 A1    6/2014    Kelly

FOREIGN PATENT DOCUMENTS

DE          699 22 976 T2    12/2005
DE    10 2006 004 123 A1    8/2007
DE          600 35 791 T2    4/2008
(Continued)

*Primary Examiner* — Ashley L Fishback
(74) *Attorney, Agent, or Firm* — Aslan Law, P.C.

(57) ABSTRACT

A system comprising a sluice and a catheter. The catheter including an inner, a middle and an outer tube. A stent is disposed in a distal-end portion of the catheter between the inner and outer-tube. The middle-tube ends distally at the proximal end of the stent. An actuating unit having a drive unit provided in the proximal region of the catheter for releasing the stent. A connecting portion is provided between the drive unit and the sluice. The drive unit is cooperating with the middle-tube and the connecting portion where the drive unit is operated the middle-tube is displaced in the distal direction and the actuating unit together with the outer-tube attached thereto is displaced in the proximal direction. The inner-tube is cooperating with the middle-tube and/or the connecting portion and/or the drive unit in such a way that the inner-tube is displaced at least to some extent relative to the actuating unit.

19 Claims, 8 Drawing Sheets

(56) References Cited

FOREIGN PATENT DOCUMENTS

STENT DELIVERY SYSTEM

The invention concerns a system for inserting a compressed, self-expandable stent through a sluice disposed on a blood vessel into the blood vessel and for releasing the stent in the blood vessel, with a catheter comprising an inner tube, a middle tube and an outer tube, whereby the inner tube runs through the middle tube and the middle tube through the outer tube. The compressed stent is radially disposed in a distal end portion of the catheter around the inner tube between the inner tube and the outer tube, and the middle tube is placed distally at the proximal end of the stent respectively ends at the proximal end of the stent. Furthermore, an actuating unit with a drive unit is located in the proximal portion of the catheter for releasing the stent. Such a system is already known from DE 10 2013 015 896 A1. Further features of the preamble of claim 1 are known from US 2014/0135909 A1.

Various types of stents are already known from the state of the art. Laser-cut stents in particular have been around for some time. However, these only conditionally adapt to a lumen and it has been learned that these tend to break in a lumen after a few years. That is why braided stents have been developed, which are not only more flexible, but also do not break after years in use in a lumen and are inexpensive to produce. These braided stents extend radially outward when released in a lumen and thus expand a lumen. However, upon release the position of the stent changes, primarily due to the change in length and diameter. These are thus more difficult to position as laser-cut stents.

Furthermore, various insertion systems, especially for braided, self-expandable stents are already known from the state of the art. These are generally catheter systems with which the stent is shifted to its place of application and thereupon expanded so that the stent is released from the catheter. Such insertion systems are used to implant vessel stents in blood vessels that have been injured or their lumen blocked or constricted due to a disease or similar cause, whereby the vessels' functionality is severely impaired.

For implantation the stent is generally radially compressed in a catheter so that its cross sectional area is greatly reduced, whereby its length is greatly increased so that it can be inserted into the vessel with relative ease. The catheter is then inserted into the blood vessel via the so-called sluice. The sluice is a catheter through which other catheters or instruments can be inserted into a patient for medical purposes. The Seldinger technique or Seldinger method is one method for puncturing blood vessels for the purpose of catheterisation (application of the sluice).

If the stent is a self-expandable stent, it expands into its original shape through its elasticity or spring effect during release, and thus stretches its lateral surface so that it inserts into the blood vessel and expands or supports the lumen of the blood vessel. This makes positioning of the stent down to the millimeter difficult even for highly experienced users. However, a precise position is absolutely desired and necessary from a medical perspective. X-ray markers are especially useful for monitoring the location of the stent.

The following invention aims to facilitate precise placement of the stent along with beneficial stent expansion.

This task is solved by a system with the features of claim 1. That is why there is a connecting means between the drive unit and the sluice. The drive unit cooperates with the middle tube in such a way that when the drive unit is operated the middle tube is pushed in a distal direction and the actuating unit, along with the attached outer tube, is pushed in a proximal direction. Furthermore, the inner tube cooperates with the middle tube and/or the connecting means in such a way that it is shifted, at least to some extent, relative to the actuating unit and thus to the outer tube. However, it is possible for the inner tube to cooperate with the drive unit in such a way that it is shifted relative to the actuating unit and thus to the outer tube.

The self-expandable stent may also be a self-expandable, braided stent or a stent made from metal wire or synthetic fibres by other means. Braided stents in particular are problematic in that they expand very drastically upon release and thus cannot take the determined position after release.

The connecting means may have a static consistency or may comprise an arrangement of static connecting means sections that can move against each other. It is thus possible for the connecting means to be designed as a telescopic rod or telescopic tube, or as a toothed rod. However, it is also possible that the connecting means is elastically pliable, for example as a wire or as a flexible toothed rod, or comprises an elastic, pliable connecting means section.

Because the drive unit is intended to be designed in such a way that, when it is operated, the middle tube moves in a distal direction and the actuating unit and the attached catheter are pushed in a proximal direction, the specified position of the distal end of the stent cannot (or can only slightly) be altered during release. The stent is thus released when the middle tube pushes the proximal end of the compressed stent forward, i.e. in a distal direction, whereas the actuating unit is moved proximally, whereby the attached catheter as well as the stent attached to the catheter are moved proximally.

At the same time the distal end of the inner tube at least to some extent retains its position when the inner tube motion-couples with the connecting means, as the actuating unit is then at least to some extent movable relative to the inner tube. The inner tube usually exhibits a tip at the distal end that tightly seals the catheter. The stent is gradually released from the catheter when, during release of the stent, the actuating unit and with it the outer tube are moved in a proximal direction, while the middle tube is moved distally and the inner tube always simultaneously retains its distal final position at the beginning of the release.

If the inner tube motion-couples with the middle tube, it moves distally with the middle tube while the outer tube moves proximally. This, too, gradually releases the stent.

The connecting means also prevents uncontrolled proximal movement of the actuating unit during release of the stent. In state of the art DE 10 2013 015 896 A1, there is no connecting means between the sluice and the drive unit so that, especially due to friction between the outer tube and middle tube, outer tube and sluice, and outer tube and blood vessel, the actuating unit is subjected to proximal momentum during release of the stent, so the operator must counteract a proximal movement of the actuating unit.

The movement of the middle tube and the actuating unit with the attached catheter may occur synchronised or alternating at the same or a different distance. Ideally there is a transmission ratio so that the movement occurs at different distances.

Overall the system of this invention ensures that after release of the stent, not only the distal end of the stent but also the proximal end takes its specified position, and thus the entire stent takes its specified position after release. The specified position may be within a certain area, in particular between 0 and 5 mm. The stent thus reaches its target length after release and thereby its overall specified position as well. Furthermore, movement of the actuating unit relative to the inner tube also facilitates a beneficial reduction in friction between the individual catheter tubes.

According to an embodiment the inner tube is motion-coupled with the middle tube. The compressed stent is thereby arranged on the inner tube in such a force-fitting manner that it is also displaced in the distal direction when the middle tube and thus the stent are displaced in the distal direction.

The inner tube, together with the middle tube, is thus hereby shifted distally to facilitate a release of the stent.

In particular it may be specified that the actuating unit exhibits a movement limitation for the inner tube to merely facilitate a movement of the inner tube relative to the actuating unit to some extent.

In particular it may be specified that the inner tube is moved distally at the beginning of the stent release in order to allow for the catheter to open in such a way that the stent can move out from the catheter. In this regard it may especially be specified that the inner tube is led in the proximal area in a guiding tube with a rinsing connection (Luer connection) and the proximal end of the inner tube is fastened onto the rinsing connection. The guiding tube can end in the actuating unit and exhibit an inhibitor led in a conduction in the actuating unit. Furthermore, the actuating unit can exhibit a complementary stop so that movement of the inner tube is merely possible to an extent, namely until the inhibitor of the guiding tube reaches the stop. Once the stop has been reached the inner tube also moves proximally. To this end, distal movement of the inner tube may be possible between 50 and 250 mm, in particular 200 mm. Overall the compressed stent can exhibit a length of 100 to 600 mm, in particular 570 mm. As a result a motion-coupling of the inner tube with the middle tube may occur for the first 200 mm movement path of the distally moving middle tube. For the remaining 300 to 400 mm, in particular 370 mm, the middle tube only moves distally while the inner tube along with the outer tube move proximally due to the movement of the actuating unit.

However, it is also possible for the inner tube to be attached to the connecting means so that the actuating unit, together with the outer tube, is moved proximally relative to the inner tube when the actuating unit is displaced.

As a result the distal end of the inner tube can retain its position, as the actuating unit, along with outer tube, is moved proximally by the interaction with the connecting means, while the inner tube retains its position due to the connection with the connecting means.

It is especially ideal if the connecting means comprises a primary and a secondary portion. The primary portion may be connected to the sluice, while the secondary portion can be fastened onto the inner tube and can interact with the drive unit. Furthermore, the two portions can be displaced relative to one another in a primary state of operation, and be connected to one another in a secondary state of operation.

As a result the connecting means may have a telescopic design and especially exhibit a primary portion designed as a wire, which is guided through a secondary portion designed as a tube in the area of the actuating unit. The two portions can be braced against one another to this end, for example by a bracing device. In particular the bracing device can be arranged in the distal area of the actuating unit in front of the actuating unit, and can be manually operable. The benefit of this lies in the fact that the portions can be displaced against one another in the primary state of operation and thus the initial distance between the actuating unit and the sluice can be set without any operation of the relocation element or the secondary portion by the drive unit, and thus no relocation of the inner tube relative to the actuating unit.

It is especially preferable if the interaction between the drive unit and the middle tube is releasable. Otherwise, or in addition to this, the interaction with the connecting means may be releasable.

Beneficially, the interaction of the drive unit with both the middle tube as well as the connecting means is releasable dependently and independently of one another. This ensures the greatest possible flexibility for the operator. In particular the operator can thus position the actuating unit before the stent is released without triggering relative movements of the catheter tubes relative to one another.

Furthermore, it is especially preferable if the drive unit is attached to a bearing section, whereby the bearing section can be pivoted so that the interaction of the drive unit with the middle tube and/or the connecting means is releasable.

In particular the bearing section may be a pivoting axis in the distal part of the actuating unit. The drive unit can specifically comprise a rotating shaft, whereby the rotating shaft can exhibit means for interacting with the connecting means or the middle tube. In particular these means may be gears or sprockets. The rotating shaft may be stored in the bearing section, with the capacity to rotate. To this end the proximal section of the bearing section at the proximal part of the actuating unit may be reversibly tightened, especially via a locking or snapping connection.

Beneficially there is a displacement element that can be motion-coupled with the inner tube. The displacement element can be arranged in an first position on the actuating unit in such a way that the bearing section pivots so that the interaction of the drive unit with the middle tube and/or connecting means is released. In a second position the displacement element can be displaced in a distal direction along the actuating unit in such a way that the bearing section can be pivoted.

A displacement of the middle tube and/or the connecting means is then only possible once the displacement element has been shifted in distal direction and thus allows the bearing section to pivot. The inner tube is thus initially distally displaced through displacement of the displacement element relative to the middle and outer tubes before the actual release of the stent commences. It can thereby be ensured that the stent has sufficient room to expand.

In particular the inner tube may exhibit a tip at the distal end, whereby the tip seals the catheter fluid-tight when the displacement element is in the first position, and whereby the catheter is open when the displacement element is in the second position.

The catheter can thus be rinsed in the fluid-tight position and then open in the second position in order to securely facilitate expansion of the stent.

According to an embodiment the bearing section exhibits a strap with a stop, whereby the displacement element in the second position rests against the stop, thereby making the bearing section pivotable.

This ensures that the inner tube, and thus the distal end of the inner tube, is displaced along a predetermined path, in particular 15 to 25 mm.

According to a preferable embodiment of the invention the proximal end of the inner tube is secured to a guide tube having a flushing connection, whereby the guide tube exhibits the displacement element. The guide tube can end in the proximal part of the actuating unit.

Furthermore, it is especially preferable if the actuating unit exhibits a pressing element that presses the middle tube and/or the connecting means for the motion-coupling against the drive unit.

In particular the pressure element may be designed as a flat spring or coil spring in conjunction with a ball bearing, especially a grooved ball bearing. This ensures a secure connection of the middle tube with the drive unit and/or the connecting means with the drive unit. This is especially beneficial if the drive unit interacts directly with the middle tube and/or the connecting means. In particular the middle hose and/or the connecting means may be pressed against the drive unit under pretension. It would also be possible for the strap of the bearing section to function as a pressure element.

Beneficially the pressure element is pivotable, so that interaction between the drive unit and the middle tube and/or the connecting means can be released.

Preferably the connecting means exhibits a fastening portion on its distal end with which the connecting means is connected to the sluice. To this end the fastening portion can exhibit a catheter guidance section that holds the sluice, in which the catheter is guided.

The interior of the catheter guidance section, as well as the entire fastening portion itself, can be made from POM or PTFE or comprise this material in order to reduce friction between the fastening portion, sluice and catheter. Other friction-reducing coatings would also be conceivable.

A stabilising element around the connecting means and/or the catheter, in particular a coil spring or a braided element, is especially preferable between the sluice and the fastening portion in order to prevent deflection of the connecting means and/or the catheter. The stabilising element thus particularly serves as bending/kink protection for the catheter as well as for the connecting means.

In relation to the invention it is also possible that a withdrawal of the only partially released stent into the catheter is possible when the drive direction of the drive unit is reversed. In particular there is the risk that the catheter section between the sluice and actuating unit can be kinked or bent by friction between the catheter and sluice. The stabilising element facilitates beneficial kink protection.

Other characteristics and beneficial embodiments of the invention can be found in the following description, with which the invention is described and explained in greater detail.

It shows:

FIG. 1: A schematic, perspective depiction of a system according to the invention according to a first embodiment; b) schematic, cut side view of a part of the system near the sluice; c) depiction as per a) but with lowered connecting means;

FIG. 2 a schematic cut view of the system as per FIG. 1a with an first drive variant (a)) and a secondary drive variant (b));

FIG. 3 an explosion display of the actuating unit of the system as per FIG. 1a;

FIG. 4 a perspective view of the proximal part of the actuating unit in an first variant (a)) and a secondary variant (b));

FIG. 5 a) a schematic, perspective partial explosion display of a system according to the invention according to a second embodiment; b) schematic lateral view of the proximal part of the system;

FIG. 6 a) a schematic, lateral view of a system according to the invention according to a third embodiment; b) schematic lateral view of a part of the system around the sluice; c) schematic lateral view of the proximal part of the system; and FIG. 7 a) a schematic, perspective depiction of a system according to the invention according to a fourth embodiment; b) schematic, perspective view of a part of the system around the drive unit according to an first variant (b)) and a secondary variant (c)).

FIGS. 1 to 4 show a system according to the invention according to a first embodiment. The system serves to insert and release a self-expandable, braided stent 2, the compressed form of which can be seen in FIG. 1b. The stent is radially constricted in this form and is much longer than the self-expandable form. Furthermore, a catheter 4 is presented with an inner tube 6, a middle tube 8, and an outer tube 10, whereby the middle tube 8 extends through the outer tube 10 and the inner tube 6 extends through the middle tube 8. The compressed stent 2 in a distal end section of the catheter 4 is radially compressed and arranged around the inner tube 6 running between the inner tube 6 and outer tube 10, whereby the middle tube 8 ends distally at the proximal end of the compressed stent.

Figure 1A:
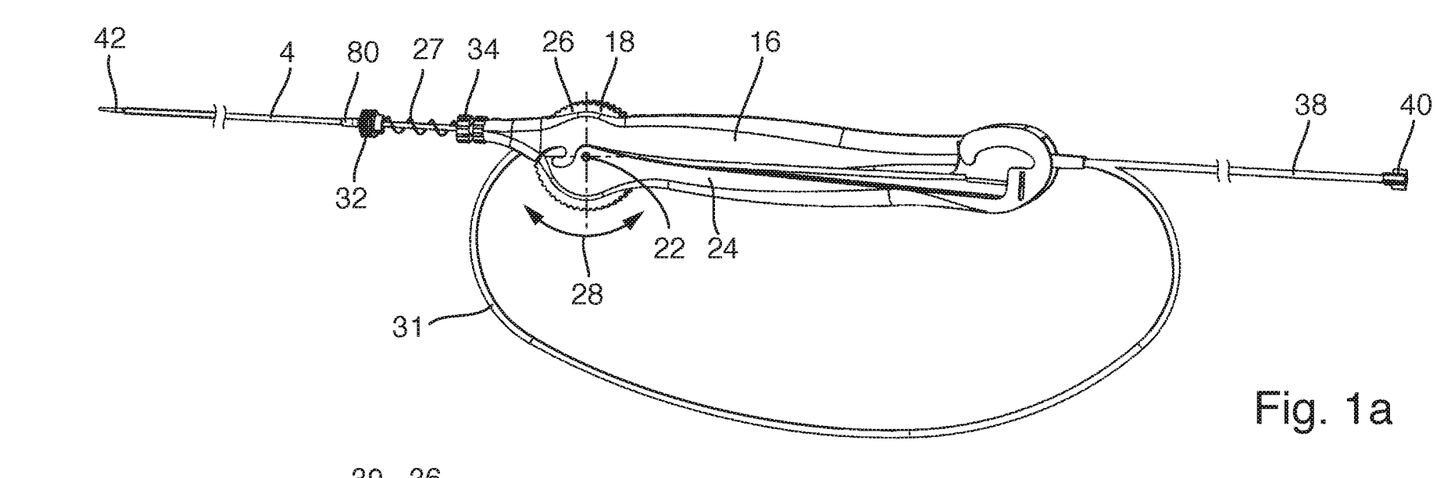
Figure 1B:
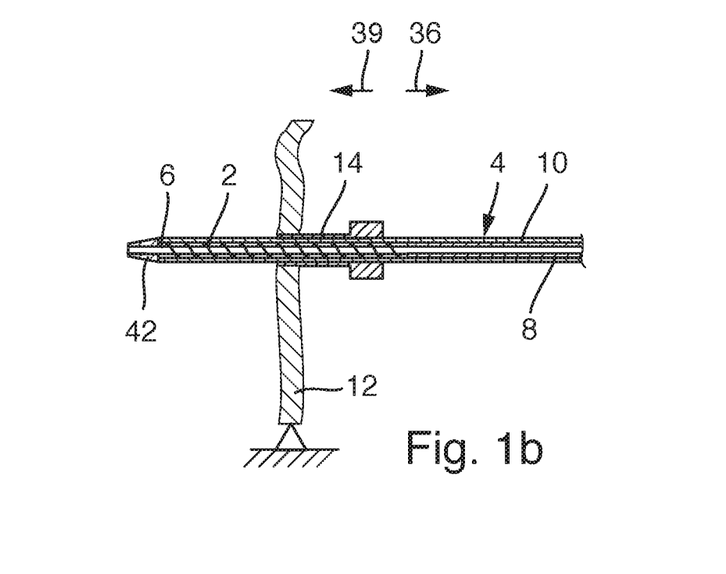

The catheter 4 is inserted into the blood vessel via a sluice 14 disposed on a blood vessel 12.

There is an actuating unit 16 containing a drive unit 18 in the proximal part of the catheter 4, outside of the blood vessel 12. The drive unit 18 includes a rotating shaft 20 visible in FIG. 2, which can rotate around a rotating axis 22 and which is housed in a bearing section 24 of the actuating unit 16, where it can be rotated. Furthermore, a dial 26 is provided on the rotating shaft 20 for manual or automated rotation of the rotating shaft 20 in the direction of rotation 28 around the rotating axis 22.

Between the drive unit 18 and the sluice 14 is a connecting means/connector 30 designed as a connecting tube. The connecting means 30 exhibits a fastening portion 32 on its distal end, with which the connecting means 30 is fastened to the sluice 14. The connecting means 30 runs in a proximal direction 36 first through the drive unit 18 and further through the actuating unit 16, and runs into an arch-shaped guide tube 31.

The fastening portion 32 exhibits a catheter guiding section 80 that braces the inside of the sluice 14. The catheter 4 is thus inserted into the blood vessel 12 via the catheter guiding section 80 of the fastening portion 32. The catheter guiding section 80 simultaneously functions as a friction inhibitor. It is coated with either POM or PTFE, or consists of one of these materials or contains one of these materials.

Between the fastening portion 32 and the actuating unit 16 is a stabilising element/stabilizer 27, in the form of a coil spring, around the catheter 4 and the connecting means 30. This especially serves as kink protection against kinking of the catheter 4 or of the connecting means 30 when pressure is applied to them.

The catheter 4 is inserted into the actuating unit 16 via the opening 34 and disposed there.

The outer tube 10 ends in the proximal direction 36 before the middle tube 8 and the inner tube 6. The proximal end of the outer tube 10 is disposed in the opening 34 of the actuating unit 16.

The inner tube 6 is led through the actuating unit 16 and ends in the proximal part of the actuating unit in a guide tube 38, which exhibits a flushing connection 40 on its proximal end. The proximal end of the inner tube 6 is fastened fluid-tight onto this flushing connection 40.

Through the flushing connection 40 liquid can be led to the distal end of the catheter 4. The inner tube 6 exhibits a tip 42 so that the outer tube 10 can be fluidly connected to the inner tube 6 in such a way that fluid can be led to the distal end of the catheter 4 via the inner tube 6, and can be drained from the catheter 4 between the outer tube 10 and the middle tube 8 and/or the middle tube 8 and the inner tube 6.

Figure 2A:
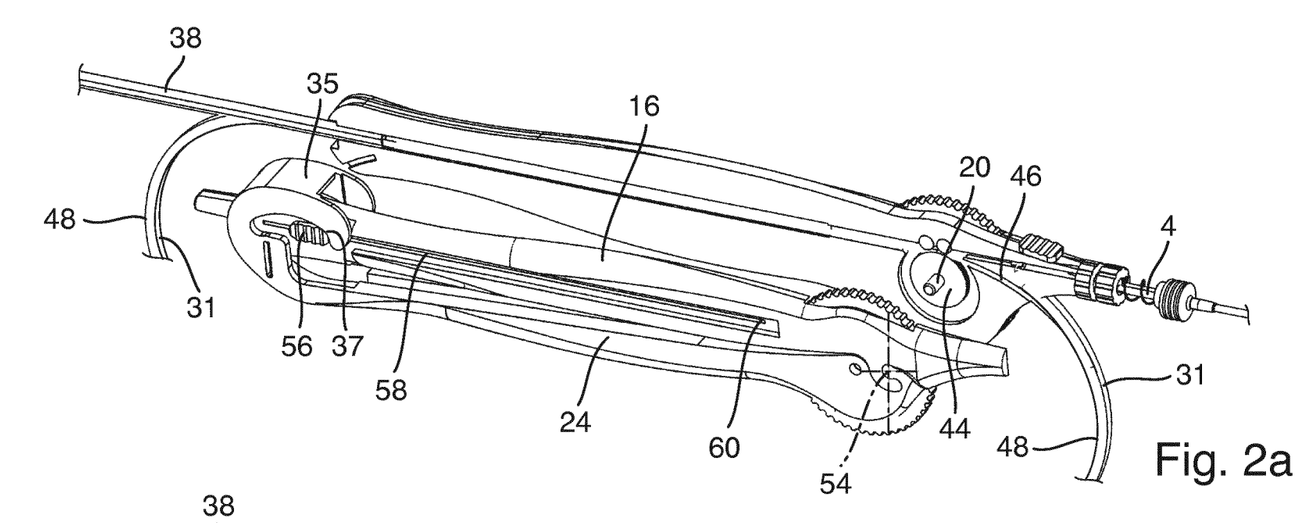

In order to drive the middle tube 8 the drive shaft 20 exhibits a drive gear 44, which is visible in FIG. 2. In particular this may be designed like a gear. It is possible for the drive gear 44 to influence a flexible toothed rod 46, shown in FIG. 2a. The proximal end of the toothed rod 46 is fastened to the proximal end of the middle tube 8. In the distal direction 39 this toothed rod 46 leaves the actuating unit 16 and moves into a second arch-shaped guide tube 48. Through rotation of the dial 26 the toothed rod 46 and thus the middle tube 8 can move in a distal direction.

Figure 2B:
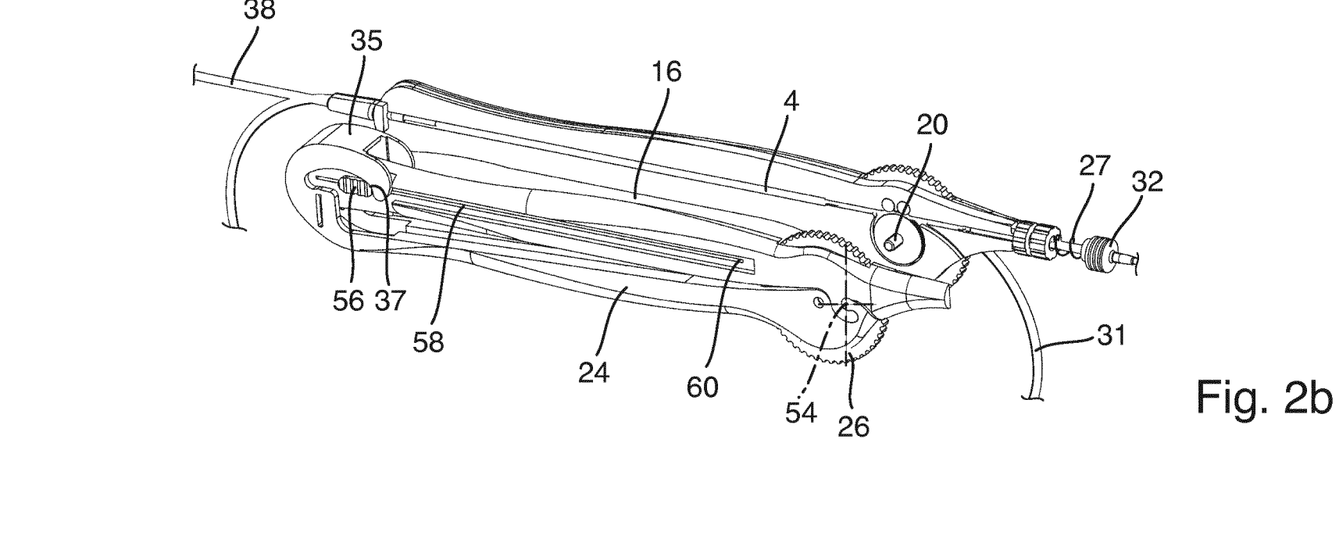
Figure 3:
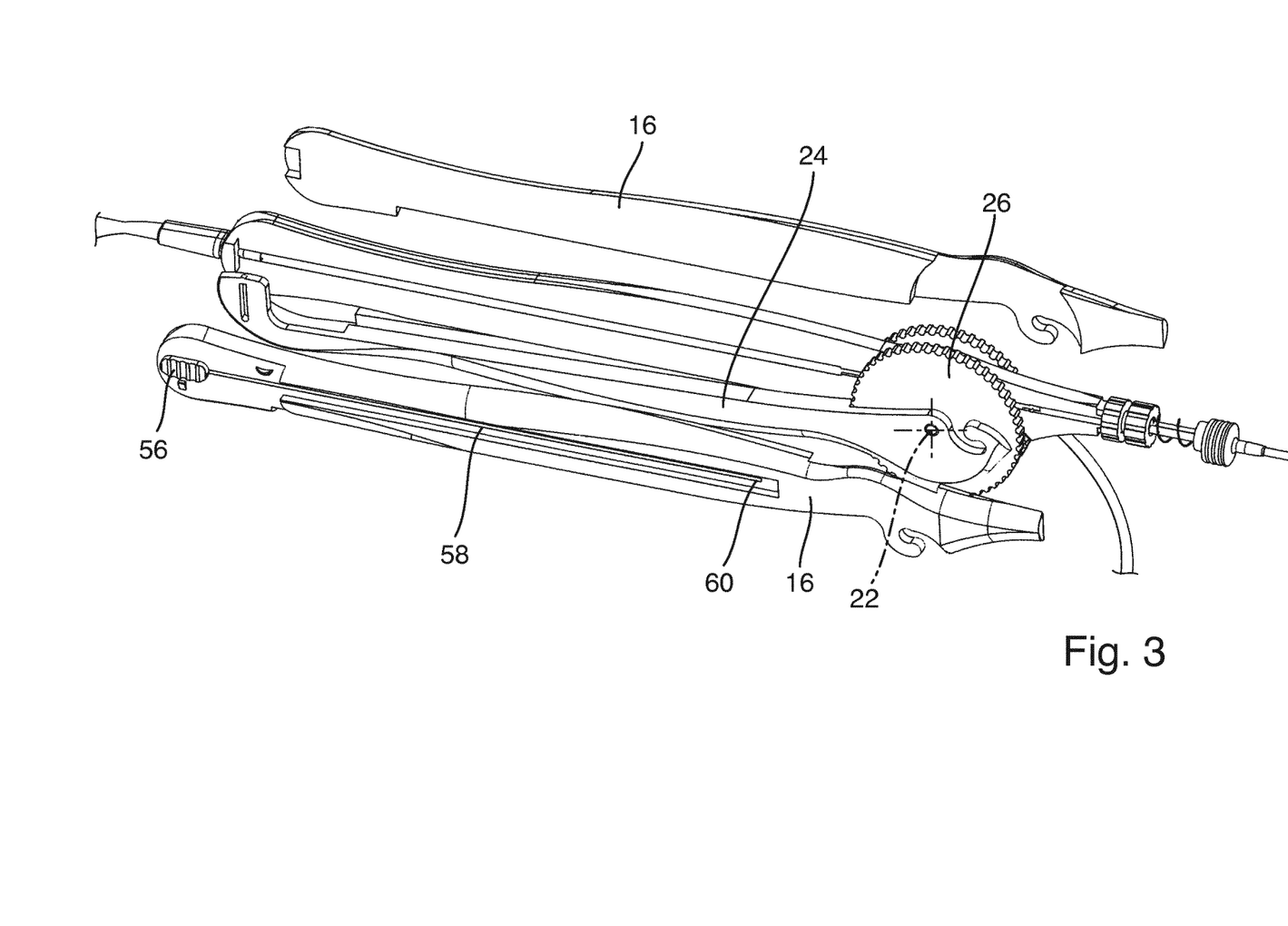

It is also possible for the drive gear 44, as depicted in FIG. 2b, to directly influence the middle tube 8. In order to ensure reliable motion-coupling a pressure element 50, 52 may be provided, which can be seen in FIGS. 7b and 7c, and which may also apply to this first embodiment of the invented system. For example, the pressure element may be in the form of a ball bearing 50 or a flat spring 52.

The pressure element 50, 52 pushes the middle tube against the drive gear 44 via elastic pretension.

Figure 5A:
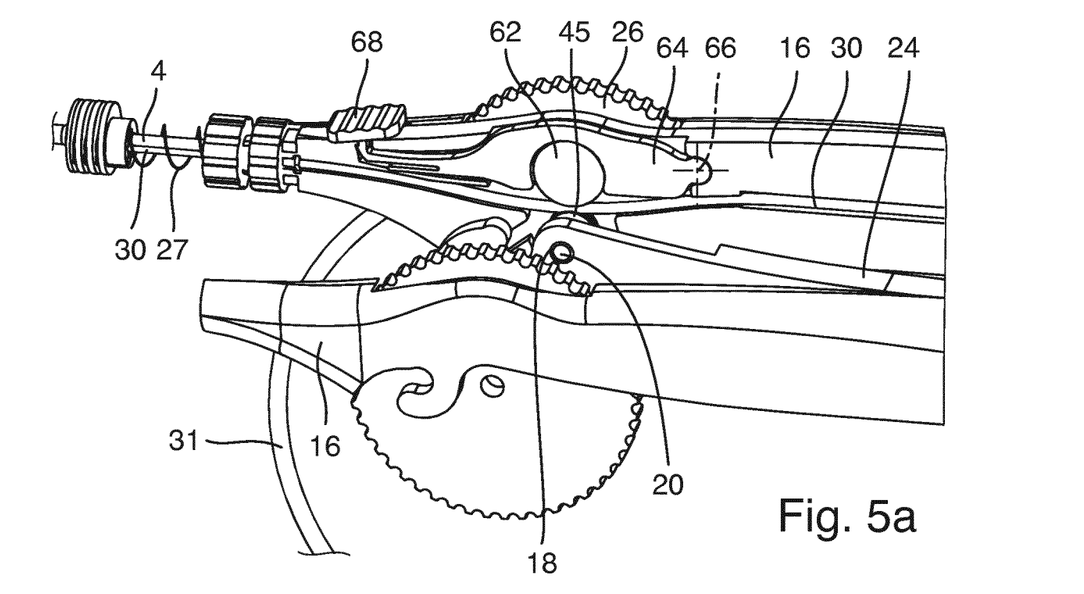
Figure 7A:
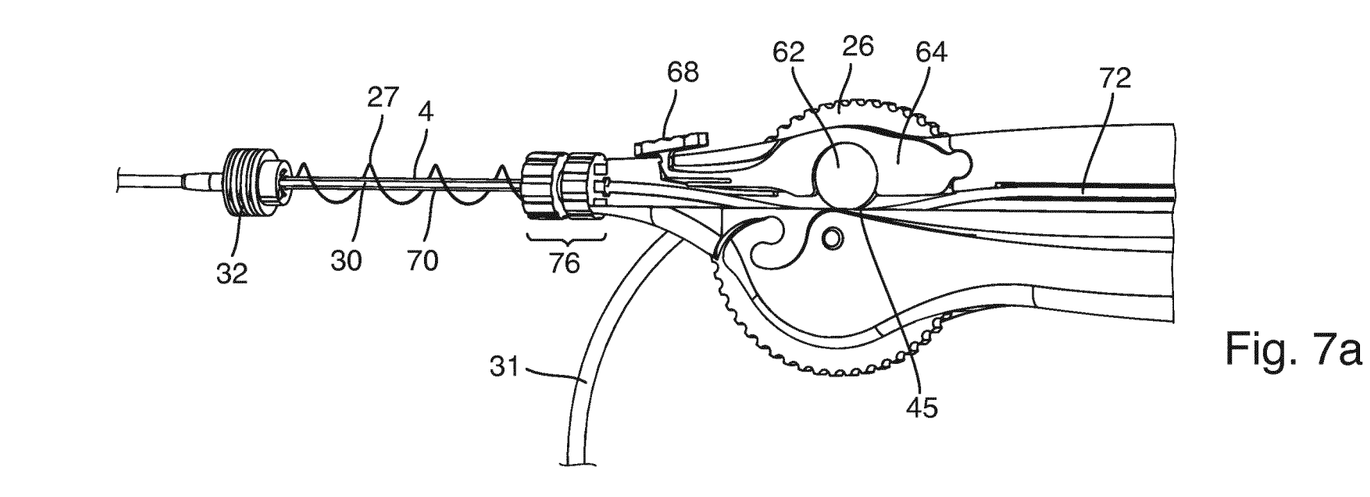
Figure 7B:
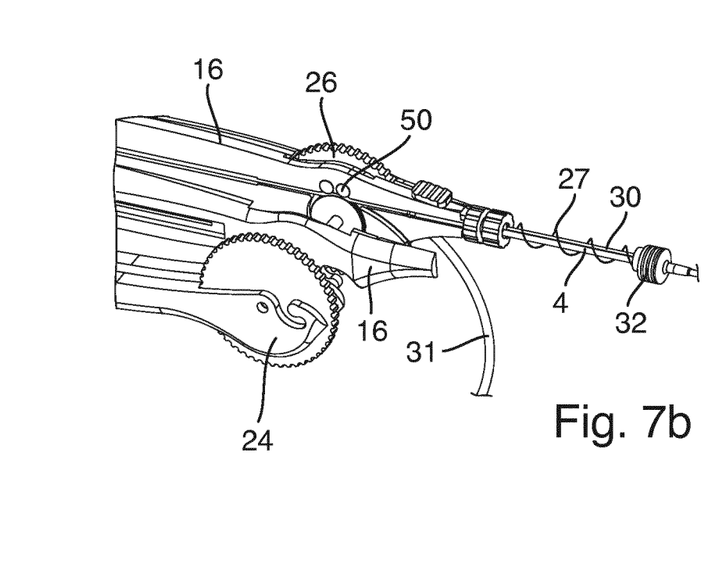
Figure 7C:
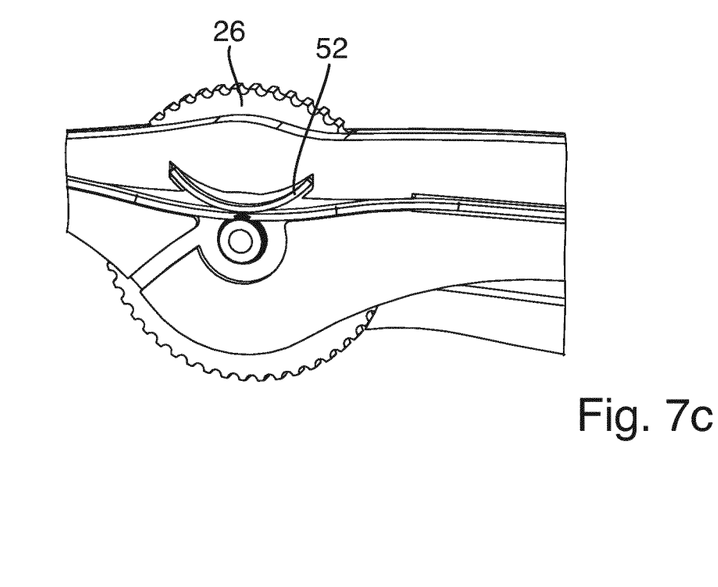

The drive shaft also exhibits a drive gear 45 (cf. 5a and 7a), which interacts either directly or indirectly with the connecting means 30.

In order to prestress the connecting means 30 and to be able to change the location of the actuating unit 16 before the release of a stent 2, the bearing section 24 can be moved in such a way that the interaction with the middle tube 8 can be released. The bearing section 24 can pivot around a pivot axis 54. The bearing section 26 is adjustably connected to the distal part of the actuating unit 16. In the pivoted position shown in FIG. 2 the dial 26 can be rotated and the actuating unit 16 can be moved in the proximal direction 36 without the middle tube 8 being simultaneously moved in the distal direction 39 by the drive gear 44.

Figure 4A:
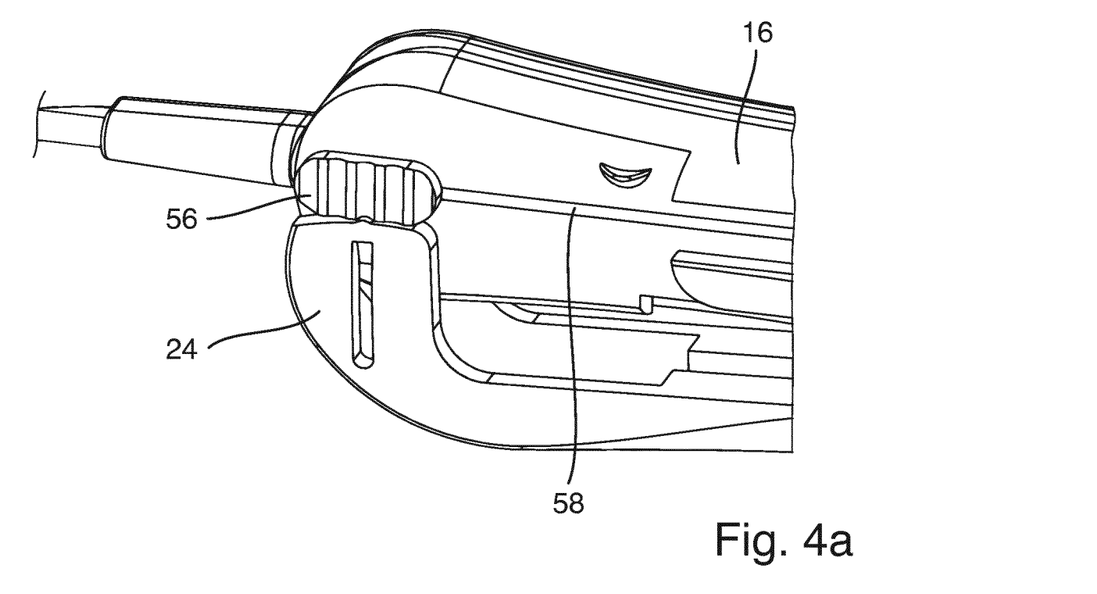
Figure 4B:
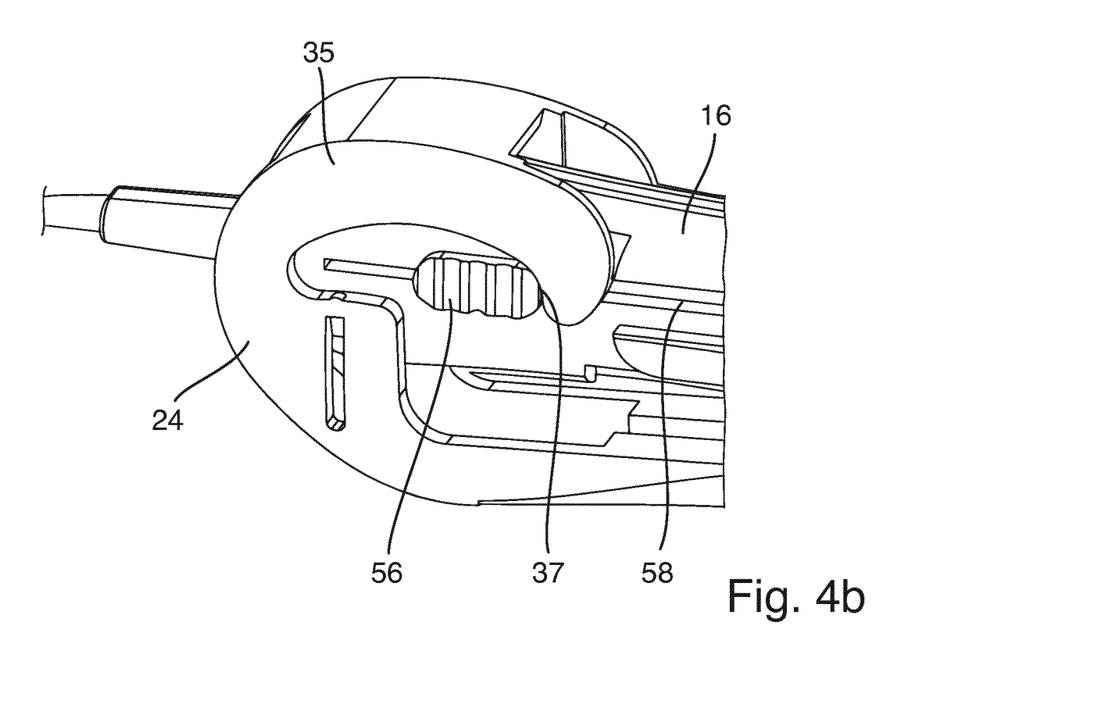

The proximal part of the actuating unit 16 includes a displacement element 56 that is fastened to the guide tube 38. This can be displaced along a guide path 58 in the actuating element 16. In the first position shown in FIG. 4a, the displacement element is located in the path at the proximal end of the path and thus prevents the bearing section 26 from pivoting. A motion-coupling between the drive unit 18 and the middle tube 8 is thus prevented. If, as shown in FIG. 4b, the displacement element 56 is displaced to a second position, the bearing section 24 can be pivoted toward the actuating unit 16, thereby creating a motion-coupling between the drive unit 18 and the middle tube 8. The bearing section 24 in the proximal part of the actuating unit 16 can be reversibly fastened to it via a lock connection that is not shown. The lock connection must be unlocked in order to pivot the bearing section 26 again. Contrary to the variant in FIG. 4a, the bearing section 24 shows a strap 35 with a stop 37 as per FIG. 4b, whereby the displacement element 56 rests against the stop 37 in the second position, so that the bearing section 24 can be pivoted.

Thus, in order to release the stent 2, the lock connection must first be made in order to facilitate interaction of the drive unit 18 with the middle tube 8. Displacement of the displacement element 56 in the distal direction 39 causes the tip 42 of the catheter 4 to be displaced in the distal direction 39, thereby opening the catheter 4 so that release of the stent is possible, especially at the beginning.

Figure 1C:
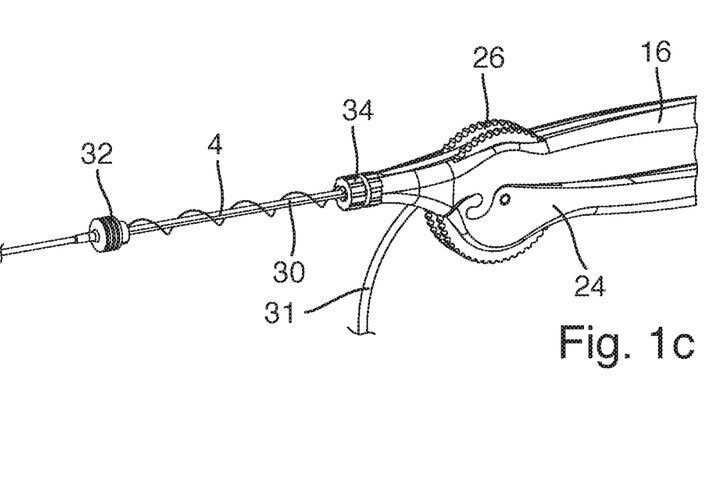

In order to release the stent 2, the dial 26 is moved counterclockwise by an operating person as per FIG. 1.

This has two results: the interaction of the drive gear 31 with the middle tube 8 moves it in the distal direction 39.

Simultaneous to this the connecting means 30 is also led out from the actuating unit 16 by an unpictured drive gear, which causes a movement of the actuating unit 16 and the outer tube 10 in the proximal direction 36. The compressed stent 2 is thus disposed between the outer tube 10 and the inner tube 6 in such a way that a shift of the middle tube 8 in the distal direction 39 also triggers a movement of the inner tube 6 in the distal direction 39. This motion-coupling is present until the displacement element 56 reaches the distal end of the guide 58, designed as a stop 60. As of this point in time the inner tube 10 will also shift in the proximal direction 36 together with the actuating unit 16. Thus, for example, a stent 2 with a length of 570 mm can be released in that the middle tube 8 is moved a total of 570 mm in the distal direction in order to release the stent 2. In particular the displacement element 56 and thus the inner tube 6 can be shifted by 200 mm. There is no further motion-coupling between the middle tube 8 and inner tube 6 for the remaining 370 mm. If the stent 2 is released, withdrawal of the displacement element 56 in the proximal direction 36 allows for the quick and controlled withdrawal of the tip 42 of the inner tube 6 through the stent.

The stent 2 is thus gradually released, whereby it retains its specified position. The distances between the relative movement of the actuating unit 42 as well as of the middle tube 8 and the sluice 14 after complete rotation of the dial 32 thus vary. This transmission ratio can be set by selecting the radii of the drive gear 44 for the middle tube 8 as well as of the drive gear for the connecting means 30, and may vary depending on the length of the stent 2.

FIG. 5 shows a second embodiment of the system. As a supplement to the first embodiment, the motion-coupling between the connecting means 30 and the drive unit 18 can also be released. A pressure element 62 is housed in a pivot part 64. The pivot part 64 can pivot around a pivot axis 66. As per FIG. 5a the pressure element 62 pushes the connecting means 30 against the drive unit 18 with the drive gear 45 for the connecting means 30 through prestress. A lock connection is also applied for pivoting, so that pulling on the lever 68 allows for the pivot part 64 can catch onto the actuating unit 16 in order to suspend motion-coupling between the drive unit 18 and the connecting means 30. An operating person can thus also manually displace the actuating unit 16 without a specified transmission ratio via the drive unit 18.

Figure 5B:
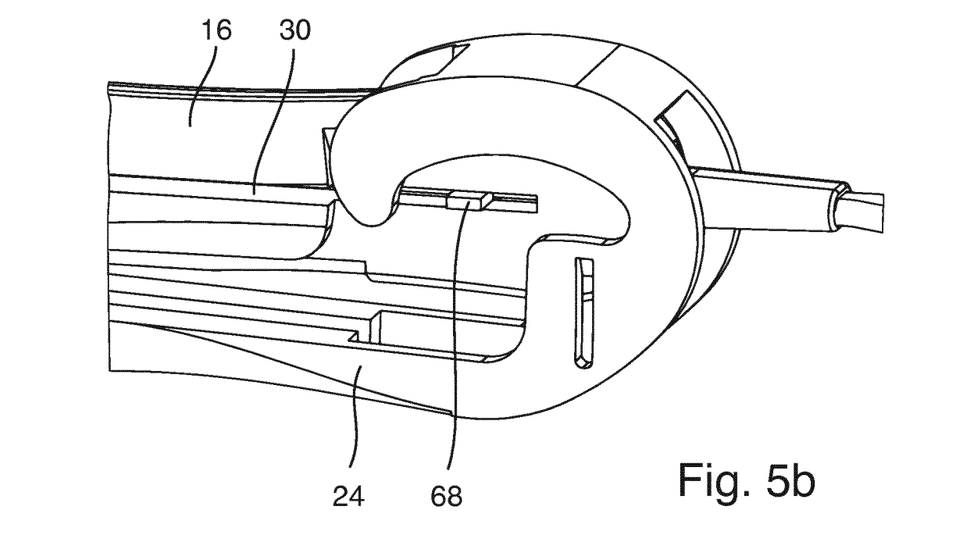

In this regard a motion-coupling may be present between the connecting means 30 and inner tube 6, as per FIG. 5b, and not between the middle tube 8 and inner tube 6. In order to be able to hereby relocate the actuating unit 16 before the release of the stent 2 without influencing the inner tube, a motion-coupling is present between the connecting means 30 and inner tube 6. A clips element 68 is located at the proximal end of the actuating unit 16 in order to create or suspend motion-coupling between the connecting means 30 and the inner tube 6. To this end it may be possible for the transmission ratio of the drive gears 44, 45 to be selected in such a way that the clips element 68 reaches the distal end of the actuating unit 16 when the stent 2 is released.

Figure 6A:
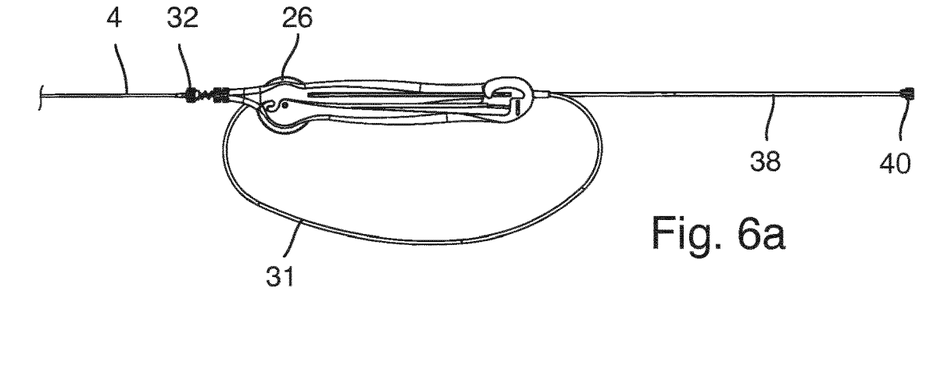
Figure 6B:
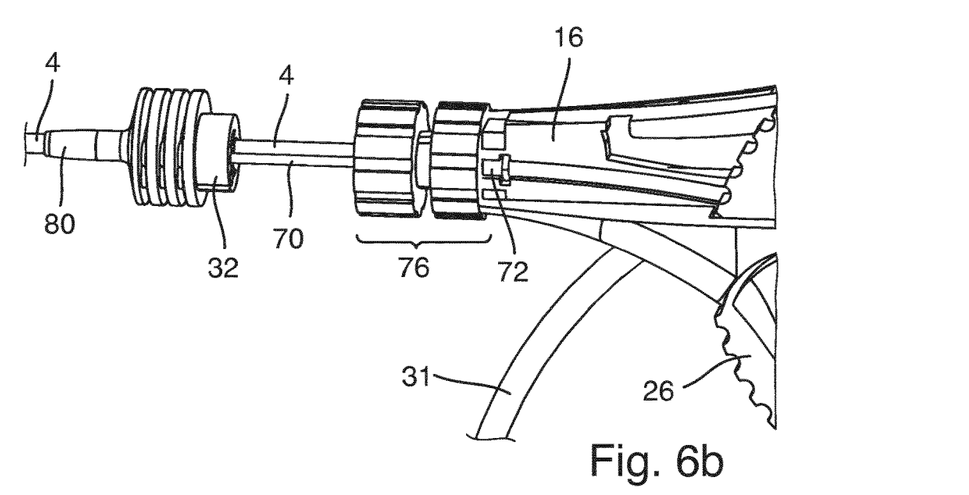
Figure 6C:
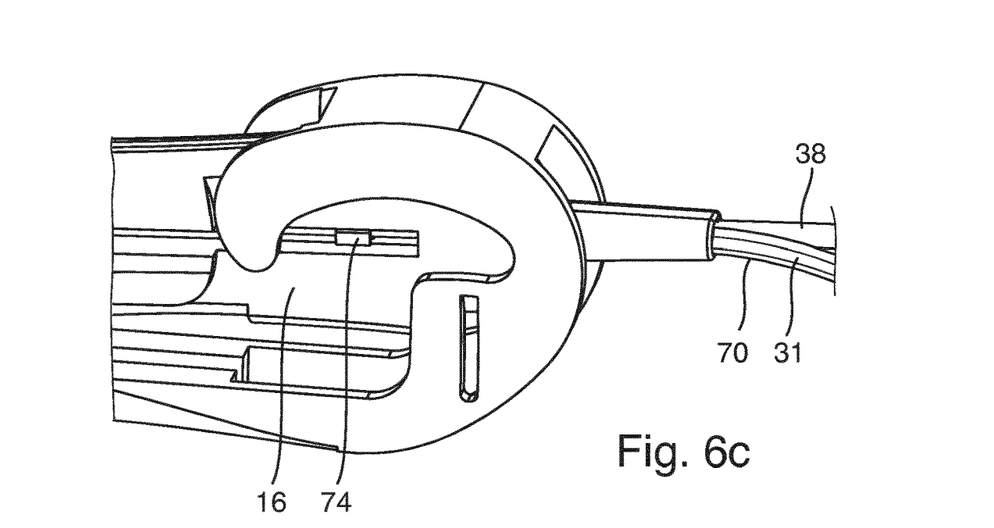

FIG. 6 shows another embodiment of the system. Here, too, there is no motion-coupling between the middle tube 8 and inner tube 6, contrary to the first embodiment as per FIGS. 1-4. There is also no opening of the tip before the release of the stent.

Instead the connecting means 30 has a two-part structure and comprises a first portion 70 in the form of connecting wire, and a secondary portion 72 in the form of a connecting tube. The first portion 70 is fastened to the sluice 14 by the fastening portion 32. The second portion 72 is connected to the inner tube 6 by a fastening means 74. The first portion 70 passes into the second portion 72 in the proximal direction 36 and passes through it. In the proximal part of the actuating unit 16 the first portion 70 enters into the guide tube 31. The second portion 72 also interacts with the drive gear of the drive unit 18.

There is a clamping device 76 in the distal end portion of the actuating unit 16 that is set so that the two portions 70, 72 can be moved against each other or can be fastened together. In a first state of operation these can be moved against each other in order to position the actuating unit 16 without causing a displacement of the inner tube 6. In a second state of operation, namely when the stent 2 is released, both portions 70, 72 are clamped against each other via the clamping device 76 and are thus fastened and motion-locked together. A movement of the connecting means 30 thus induces a displacement of the actuating unit 16 relative to the inner tube 6, so that it retains its position while the middle tube 8 and the outer tube 10 are displaced relative to it. It may also be possible for the transmission ratio of the drive gears 44, 45 to be set so that the clamping device 76 then reaches the distal end of the actuating unit 16 when the stent 2 is released.

FIG. 7 shows another embodiment of the system. Building on the system as per FIG. 6, the motion-coupling between the connecting means 30 and the drive unit 18 is releasable. As already shown in FIG. 5, a pivot part 64 with a pressure element 62 is provided to this end.

Figure 8:
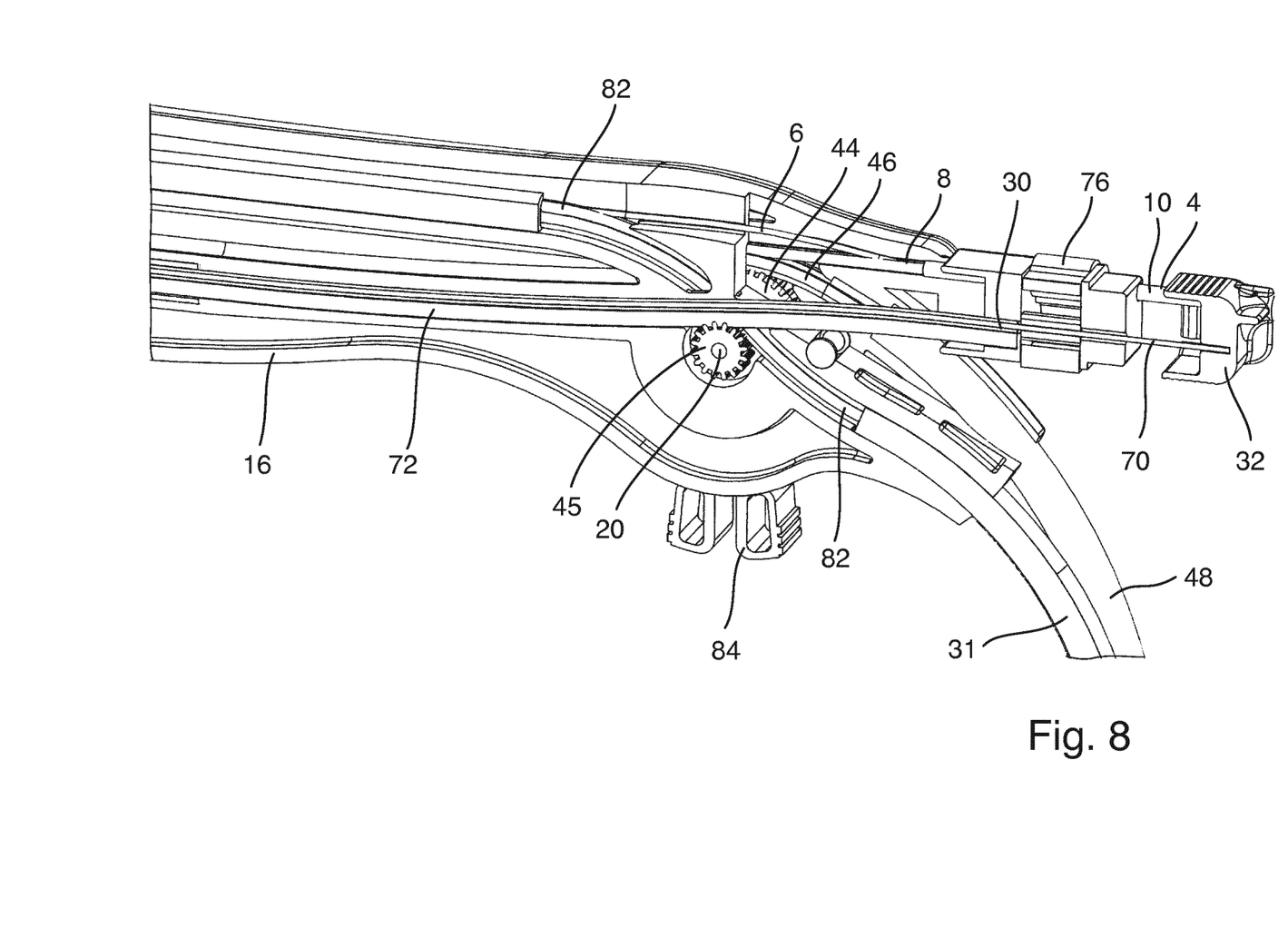
FIG. 8 Schematic, partially cut, perspective top view of a system according to the invention according to a fifth embodiment with the system's actuating unit in delivery condition.

FIG. 8a shows another embodiment of the invented system.

Building on the design as per FIG. 6, the inner tube 6 is fastened fluid-tight, but not statically, to the guide tube 38. Furthermore, the inner tube is not directly motion-coupled with the connecting means 30. The middle tube 8 is also driven by the toothed rod 46, similar to the example embodiment as per FIG. 2a.

Instead the inner tube 6 is motion-locked in the actuating unit 16 and driven by a slotted drive tube 82. The drive tube 82 is actuated by the drive gear 45 for the connecting means 30. However, it would also be possible for a separate drive gear to be provided. The drive tube 82 thus enters into the arch-shaped guide tube 31. It would also be possible to use a flexible toothed rod to drive the inner tube 6, similar to the toothed rod 46 for the middle tube 8. As is clearly shown in FIG. 8, the middle tube 8 is slotted in sections so that the inner tube 6 within the actuating unit 16 is inserted into the middle tube 8 after leaving the drive tube 82.

FIG. 8 shows the actuating unit 16 in delivery condition, i.e. before usage in the invented system. A blocking element 84 is clipped onto the actuating unit 16. The blocking element 84 influences the drive gear 44 with an unpictured toothed rod segment, namely in such a way that rotation of the dial 26 and thus the rotating shaft 20 is completely prevented. In order to be able to use the actuating unit 16 in the system, the blocking element 84 is compressed so that the clip connection is unlocked. Then the dial 26 can be turned to release the stent.

In all embodiments the middle tube 8 may exhibit a stent grasping element that elongates it and which grasps the stent 2 in such a way that the stent 2 can withdraw into the catheter 4 if it is not yet completely released. In order to release the stent 2, the dial 26 thus need only be turned in the opposite direction 28.

Overall the invention facilitates the precise release of a stent 2 in a blood vessel 12. The system also allows for one-handed, right-handed and left-handed operation.

The invention claimed is:

1. A system for inserting a compressed, self-expandable stent through a sluice disposed on a blood vessel into the blood vessel and for releasing the stent in the blood vessel, the system comprising:
a sluice; and;
a catheter, said catheter including:
are inner tube,
a middle tube, and
an outer tube, wherein
the stent is configured to be disposed in a distal end portion of the catheter between the inner tube and the outer tube and the middle tube ends distally at the proximal end of the stent, and with an actuating unit having a drive unit provided in the proximal region of the catheter for releasing the stent, wherein a connector is provided between the drive unit and the sluice, wherein the drive unit cooperates with the middle tube and the connector in such a way that when the drive unit is operated, the middle tube is displaced in a distal direction and the actuating unit together with the outer tube attached thereto is displaced in a proximal direction, and wherein the inner tube cooperates with the middle tube and/or the connector and/or the drive unit in such a way that the inner tube is displaced at least to some extent relative to the actuating unit.

2. The System according to claim 1, wherein the inner tube is motion-coupled with the middle tube, wherein the compressed stent is arranged on the inner tube in such a force-fitting manner that it is also displaced in the distal direction when the middle tube and the stent are displaced in the distal direction.

3. The System according to claim 2, wherein the actuating unit has a movement limitation for the inner tube so that movement of the inner tube relative to the actuating unit is only possible to some extent.

4. The System according to claim 1, wherein the inner tube is attached to the connector so that the actuating unit together with the outer tube is moved upon its displacement in a proximal direction relative to the inner tube.

5. The System according to claim 4, wherein the connector comprises a first portion and a second portion, wherein the first portion is fixed or is fixable to the sluice, wherein the second portion is fixed to the inner tube and is cooperating with the drive unit, and wherein the two portions are displaceable relative to one another in a first operating state and are fixed to one another in a second operating state.

6. The System according to claim 1, wherein the inner tube is displaceable relative to the actuating unit by means of the drive unit.

7. The System according to claim 6, wherein the interaction of the drive unit with the middle tube and/or the connector is releasable.

8. The System according to claim 7, wherein the drive unit is arranged on a bearing section, wherein the bearing section is pivotable so that the interaction of the drive unit with the middle tube and/or the connector is releasable.

9. The System according to claim 8, wherein a displacement element is motion-coupled with the inner tube, wherein in a first position the displacement element is arranged on the actuating unit such that the bearing section is pivoted, the bearing section being pivoted such that the interaction of the drive unit with the middle tube and/or the connector is released, and that in a second position the displacement element is displaced along the actuating unit in a distal direction such that the bearing section is pivotable.

10. The System according to claim 9, wherein the inner tube has a tip at the distal end, wherein the tip closes the catheter fluid-tight when the displacement element is in the first position, and wherein the catheter is open when the displacement element is in the second position.

11. The System according to claim 10, wherein the bearing section has a bracket with a stop, wherein the displacement element rests against the stop in the second position, and then the bearing section is pivotable.

12. The System according to claim 11, wherein the proximal end of the inner tube is secured to a guide tube having a flushing connection, wherein the guide tube comprises the displacement element.

13. The System according to claim 12, Wherein the actuating unit has a pressing/pressure element which presses the middle tube and/or the connector against the drive unit for movement coupling.

14. The System according to claim 13, wherein the pressing/pressure element is pivotable so that the interaction of the drive unit with the middle tube and/or the connector is releasable.

15. The System according to claim 14, wherein the connector has at its distal end a fastening portion with which the connector is or can be fastened to the sluice, wherein the fastening portion has a catheter guide portion which extends through the sluice in the fastened state and in which the catheter is guided.

16. The System according to claim 15, wherein a stabilizer extending around the connector and/or the catheter, is provided between the sluice and the fixing section for preventing the connector and/or the catheter from bending.

17. The System according to claim 16, wherein the stabilizer is a spiral spring.

18. The System according to claim 16, wherein the stabilizer is a braided element.

19. A system for inserting a compressed, self-expandable stent through a sluice disposed on a blood vessel into the blood vessel and for releasing the stent in the blood vessel, the system comprising:
a sluice;
a catheter, wherein said catheter includes:
an inner tube,
a middle tube, and
an outer tube, wherein
the stent is configured to be disposed in a distal end portion of the catheter between the inner tube and the outer tube and the middle tube ends distally at the proximal end of the stent, and with an actuating unit having a drive unit provided in the proximal region of the catheter for releasing the stent, wherein a connector is provided between the drive unit and the sluice, wherein the drive unit cooperates with the middle tube and the connector in such a way that when the drive unit is operated, the middle tube is displaced in a distal direction and the actuating unit together with the outer tube attached thereto is displaced in a proximal direction, and wherein the inner tube cooperates with the middle tube and/or the connector and/or the drive unit in such a way that the inner tube is displaced at least to some extent relative to the actuating unit.

* * * * *